(12) United States Patent
Layrolle et al.

(10) Patent No.: US 6,733,503 B2
(45) Date of Patent: May 11, 2004

(54) METHOD FOR COATING MEDICAL IMPLANTS

(75) Inventors: Pierre Jean François Layrolle, CT Utrectht (NL); Klaas de Groot, El Heemstede (NL); Joost Dick de Bruijn, AG Den Haag (NL); Clemens A. van Blitterswijk, PD Hekendorp (NL); Yuan Huipin, AA Zeist (NL)

(73) Assignee: IsoTis N.V., Bilthoven (NL)

( * ) Notice: Subject to any disclaimer, the term of this patent is extended or adjusted under 35 U.S.C. 154(b) by 0 days.

(21) Appl. No.: 09/757,344

(22) Filed: Jan. 9, 2001

(65) Prior Publication Data

US 2001/0053406 A1 Dec. 20, 2001

Related U.S. Application Data

(63) Continuation of application No. 09/351,518, filed on Jul. 12, 1999, now Pat. No. 6,207,218.

(30) Foreign Application Priority Data

Sep. 15, 1998 (EP) .............................................. 98203085

(51) Int. Cl.[7] .......................... A61L 27/00; A61L 27/12; A61L 27/58

(52) U.S. Cl. ............................. 606/77; 606/76; 623/16; 623/17; 623/18; 623/19; 623/20; 623/21; 623/22; 623/23; 427/2.24; 427/2.26; 427/2.27

(58) Field of Search .............................. 427/2.24, 2.26, 427/2.27; 606/76, 77; 623/16–23

(56) References Cited

U.S. PATENT DOCUMENTS

| | | | | |
|---|---|---|---|---|
| 5,068,122 A | * | 11/1991 | Kokubo et al. | ................ 427/2 |
| 5,125,971 A | * | 6/1992 | Nonami et al. | ............... 106/35 |
| 5,141,576 A | * | 8/1992 | Shimamune et al. | ........ 148/254 |
| 6,069,295 A | * | 5/2000 | Leitao | .......................... 623/11 |
| 6,139,585 A | * | 10/2000 | Li | ........................... 623/23.57 |

* cited by examiner

Primary Examiner—Shrive P. Beck
Assistant Examiner—Jennifer Kolb Michener
(74) Attorney, Agent, or Firm—Banner & Witcoff, Ltd.

(57) ABSTRACT

The present invention relates to a method for coating a medical implant, wherein the implant is submersed in an aqueous solution of magnesium, calcium and phosphate ions through which a gaseous weak acid is passed, the solution is degassed, and the coating is allowed to precipitate onto the implant. The invention further relates to a medical implant coated in said method and to a device for use in said method.

19 Claims, 9 Drawing Sheets

METHOD FOR COATING MEDICAL IMPLANTS

This is a continuation of U.S. patent application Ser. No. 09/351,518, filed Jul. 12, 1999, now U.S. Pat. No. 6,207,218.

FIELD OF THE INVENTION

The invention relates to a method for coating implant materials with carbonated calcium phosphate films. More in particular, it is concerned with the use of carbon dioxide gas—a weak acid—to decrease the pH of aqueous supersaturated calcifying solutions and deposit carbonate containing calcium phosphate layers onto implants during the natural release of carbon dioxide gas at physiological temperature. Furthermore, the invention describes a new coating method for improving biocompatibility and bone-bonding properties of medical implants, such as orthopedic and dental prostheses.

BACKGROUND OF THE INVENTION

Calcium phosphates are the principal constituent of hard tissues like bone, cartilage, tooth enamel and dentine. Naturally occurring bone minerals are made of sub-micrometer, poorly-crystalline carbonated calcium phosphate crystals with hydroxyapatite structure. However, unlike the synthetic and ideal stoichiometric hydroxyapatite $Ca_{10}(PO_4)_6(OH)_2$ with atomic Ca/P ratio of 1.67, the composition and crystallinity of bone mineral is significantly different. Bone minerals consist mainly of a complex mixture of calcium ions, phosphate ions, carbonate ions, and hydroxyl ions and may be represented by the following formulae:

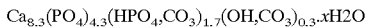

$$Ca_{8.3}(PO_4)_{4.3}(HPO_4,CO_3)_{1.7}(OH,CO_3)_{0.3} \cdot xH_2O$$

It has been demonstrated that calcium phosphate coatings on metal implants allow a rapid bone apposition due to their osteoconductive property, as compared with bare implants, e.g. cemented-less proximal hip stems. In vivo and in contact with body fluids, a thin layer of biological hydroxyl carbonated apatite is formed on the surface of some implants, like bioactive glasses, hydroxyapatite ceramics. Subsequently, living bone tissue is directly apposite to this HCA layer. The direct bone apposition onto and/or growth into the implant surface conduct to some advantages such as a firm and immediate implant fixation and long term result.

Several techniques, such as plasma spraying, flame spraying, electrophoretic deposition, magnetron sputtering and dipping, have been developed for coating hydroxyapatite and others calcium phosphates onto implants. The most conventional coating method is plasma spraying.

A drawback of most hydroxyapatite-coated implants is that the anchoring of hydroxyapatite onto the implant requires elevated processing temperatures, which limit the choice of substrate materials and result in high processing costs. In the plasma-spraying process, the raw material i.e. hydroxyapatite, is once molten at a high temperature so that the resulting apatite coatings are different in type from bone apatite. The coatings are frequently thick and brittle and are subjected to fracture at the interface between coating and implant, e.g. between hydroxyapatite and titanium, thereby releasing large particles in the body. Moreover, the method is rather unsuitable for numbers of polymer substrates because of the high temperature involved. Furthermore, it is not possible to incorporate biologically active agents, like proteins or antibiotics, within the coating, which may be useful to encourage bone in-growth or to prevent infection.

Additionally, most of these coatings are produced in a line of sight process, thereby prohibiting uniform application of hydroxyapatite on implants with complex surface geometry (e.g. porous surface). The previous methods have low efficiency for small and round-shaped substrates such as metallic dental implants.

The aim of the present invention is to provide a simple method for coating an implantable device with a thin, dense and bioactive layer of carbonated calcium phosphate. The said layers are processed at ambient temperature by soaking the implantable devices into a calcifying solution where carbon dioxide gas is passed through. The produced bioactive coatings result in effective bone apposition and in-growth and thereby ensure bone-bonding properties to the implants. The implantable device can be used in a wide variety of biomedical applications (surgery, bone-replacement, prosthodontics, dental roots, crowns and orthopedic joints, etc).

RELEVANT LITERATURE

The solubility products of the different calcium carbonate phosphate compounds are described as a function of pH, carbon dioxide partial pressure and temperature in the publication of G. Vereecke and J. Lemaitre, "Calculation of the solubility diagrams in the system $Ca(OH)_2$—$H_3PO_4$—$KOH$—$HNO_3$—$CO_2$—$H_2O$" J. Crystal Growth 104 (1990) 820–832 and in the contribution of F. C. M. Driessens entitled "Formation and stability of calcium phosphates in relation to phase composition of the mineral of calcified tissue" in Calcium Phosphate Bioceramics, edited by K. de Groot, CRC Press (1984).

The publication of P. Serekian entitled "Hydroxyapatite coatings in othopaedic surgery" edited by R. G. T. Geesink and M. T. Manley, Raven Press Ltd, New York (1993), p 81–97, discusses the advantages and drawbacks of plasma and flame spraying, electrophoresis, dip coating and magnetron sputtering.

EP No. 0 389 713 B1 (Kokubo, 1989) describes a process for applying a bioactive hydroxyapatite film on implant substrates of inorganic, metallic or organic material, by soaking an assembly comprising a glass, mainly comprising $CaO$ and $SiO_2$, facing a substrate at a predetermined distance apart, in an aqueous solution substantially saturated or supersaturated with constituent ions of hydroxyapatite. In the method according to the present invention, it is not necessary to provide an assembly of glass facing the substrate to be coated.

EP No. 0 450 939 A2 and corresponding U.S. Pat. Nos. 5,164,187 and 5,188,670 (Norian, 1990,1991) describe a complicated process and apparatus for coating porous substrates with a hydroxyapatite film. This method comprises combining a soluble calcium ion source and a soluble phosphate ion source, wherein the molarity of the calcium ions is in the range of about 0.05–5 M, the molarity of the phosphate ions is in the range of about 0.01–1 M, at the temperature of 60–90° C. and pH of 5–8.5, under conditions leading to controlled nucleation and modulated growth of hydroxyapatite needle-like crystals. Basically, one solution is injected into a circulating medium, resulting in the precipitation of hydroxyapatite whiskers or single-crystals that reach and cover the surface to be coated. This prior art method has two important drawbacks. First, hydroxyapatite crystals precipitate in the solution. On the opposite, in the method according to the invention, crystals nucleate directly on the implant surface leading to superior interfacial attachment. Second, the coating, as described in the above process, is made by stacking hydroxypatite crystals through a fluid stream which is essentially a line of sight process and thereby giving shadows effects on complex shaped surfaces. In the present invention, the deposition of carbonated calcium phosphate layers is not dependent on the direction of fluid flow.

International patent application WO A,93 07912 (Sherwood Medical, 1993) describes a bioimplant obtained by soaking a base material to be coated in a saturated or supersaturated solution of hydroxyapatite. The base material has been previously provided with an organic polymer containing sulfonic or carboxyl groups. In the method according to the invention, it is not necessary to first provide the implant to be coated with such an organic coating.

International patent application WO 95 13101 (de Groot, 1993) teaches a method for coating an implant substrate with a bioactive material represented by the general formula $Ca_p(PO_4)_q(CO_3)_r(OH)_s$ in which p>1 and q, r and s>0, and in which 2p=3q+2r+s. The said substrate is soaked in a solution in which at least calcium ions, preferably carbonate ions, and if required, phosphate ions are present, after which the bioactive material is precipitated from the solution on the substrate by either heating the solution or the substrate. In the present invention, the temperature is fixed within the range 5–50° C. and there is no need to heat the solution or the substrate to induce the precipitation of calcium phosphate. Moreover, the feasibility and bioactivity of such a coating has not been experimentally demonstrated in the International Patent Application WO 95 13101.

EP No. 0 678 300 A1 (Kokubo, 1994) discloses a process for producing a bone substitute material. In essence, a primary surface layer of a titanium oxide phase and amorphous phases of alkali titanates are formed by soaking a base material made of titanium or its alloy in an alkali solution and heating the base material to temperature lower than the transition point e.g. 300–800° C. Subsequently, the alkali- and heat-treated base material is immersed in aqueous solution which contains calcium and phosphorus ions to a level of, at least the apatite solubility, and thus producing a second layer comprising apatite on top of the said primary surface layer.

The patent applications EP 972011425/2, U.S. Pat. No. 8,855,835 and Canada 2,205,107 (Isotis BV) describe a nanotechnology process for implant surface treatment which can subsequently induce the precipitation of calcium phosphate layers by soaking in a calcifying solution. The implantable devices have a surface roughness before coating with an average peak distance between 10 and 1000 nm to induce the precipitation of calcium phosphate layers.

Japanese patent application 08040711 discloses a process for forming a hydroxy apatite coating, wherein calcium phosphate is dissolved in a solution containing sodium hydroxide, by applying high pressure carbon dioxide gas. The coating is deposited by discharge of carbon dioxide gas. In this known process, sodium hydroxide is present in the calcifying solution, which significantly increases the pH. As a result, a high pressure of carbon dioxide is needed in order to obtain a low enough pH to dissolve sufficient calcium phosphate.

SUMMARY OF THE INVENTION

The object of the present invention is to provide a simple method for coating the surface of medical implants with bioactive carbonated calcium phosphate layers. The said coatings are produced by soaking the implantable devices into highly concentrated calcifying solutions at low temperature. The calcifying solutions are composed of calcium, phosphate, magnesium, carbonate and additionally sodium chloride salts dissolved into water by bubbling carbon dioxide gas. During the natural release of carbon dioxide gas or its exchange with air, the pH of the calcifying solution is increased and the saturation is raised until the nucleation of carbonated calcium phosphate crystals on the surface of implantable devices. The said layer deposited and growth onto the medical implants. The process of bubbling/releasing $CO_2$ gas through or from calcifying solutions can be repeated until a sufficient thickness has been reached. The present invention has the following advantages over conventional coating techniques: it is simple and cost-effective approach, no expensive and intricate pieces of equipment are needed. It is a low temperature process applicable to various substrates. Further, it has been found that materials can be deposited on a substrate in the present process, which was hitherto impossible. Octacalcium phosphate coatings, for instance, cannot be prepared with conventional plasma spraying techniques, due to the heat instability of the coating material. Such coatings also have been found not to grow in epitaxial fashion when employing other coating techniques.

As the coating is applied by using a fluid, complex shaped implants (porous or beaded surfaces) can be uniformly covered with a thin layer of carbonated calcium phosphate. The obtained layer is strong and wear resistant. The said layer is formed by using a biomimetic approach (physiological fluids, temperature and pH) and thus, a bone-like apatite layer having a high reactivity and adsorption property is deposited on the surface of medical implants. The biocompatibilty and bone-bonding properties of such coated devices have been demonstrated by implantation in animal models.

DESCRIPTION OF SPECIFIC EMBODIMENTS

Figure 1:
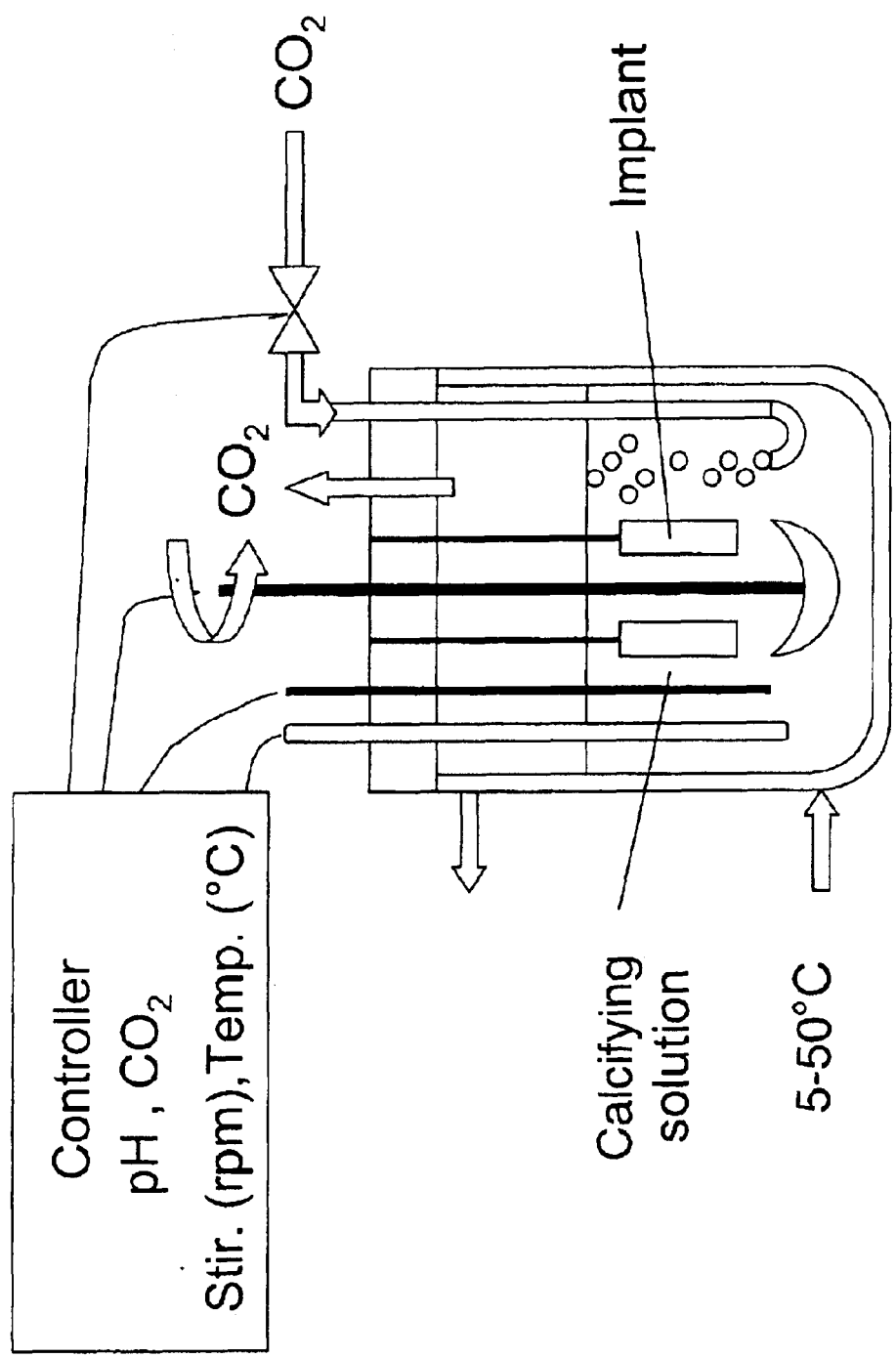
FIG. 1. Bioreactor for producing the bioactive carbonated calcium phosphate coating FIG. 2. pH changes and temperature as a function of soaking time in the calcifying solution and in pure water FIG. 3. SEM photomicrograph of the metal surface (Ti6Al4V) coated with the bioactive carbonated calcium phosphate layers FIG. 4. XRMA spectra of the carbonated calcium phosphate coating on Ti6Al4V FIG. 5. SEM photomicrograph of a porous tantalum implant coated with the carbonated calcium phosphate layers FIG. 6. XRMA spectra of the bioactive carbonated calcium phosphate coating on porous tantalum implant FIG. 7. FT-IR spectra of the bioactive carbonated calcium phosphate layers recorded on Ti6Al4V implant FIG. 8. TF-XRD pattern of the carbonated calcium phosphate on Ti6Al4V implant FIG. 9. SEM photomicrograph of a Ti6Al4V surface covered with calcium phosphate layer deposited using a calcifying solution not containing magnesium ions

The bioactive carbonated calcium phosphate layers may be applied to any medical implant, inorganic, metallic or organic materials. The implant may be flat, dense or of a complex shape. It may have a porous, beaded or meshed ingrowth surface.

Metals, such as stainless steel, titanium, nickel, cobalt, chrome, niobium, molybdenum, zirconium, tantalum, and combinations thereof, can be coated with the carbonated calcium phosphate layers for orthopaedic and dental applications. For example, devices used in total hip arthroplasty such as porous or non-porous acetabular cups and the proximal region of hip stems may be coated with the bioactive carbonated calcium phosphate layers.

Ceramic materials, such as alumina and zirconia, glasses such as bioactive glasses made of $CaO—SiO_2—P_2O_5$, and calcium phosphates, such as hydroxyapatite and tricalcium phosphate, may be coated with the bioactive carbonated calcium phosphate layers.

The subject coatings can be applied to various polymers and plastics, more preferably biocompatible or bioresorbable ones like polyactive™.

Before applying the coating, the substrates are preferably cleaned or treated to remove any surface contaminants and to promote good adhesion of the coating. Various methods for cleaning may be employed. The metallic implants may be rinsed with a degreaser, i.e. acetone, alkyl alcohols, etc. and then thoroughly rinsed with pure water.

In order to improve coating adhesion, various surface treatments may be applied to metal implants. Mechanical surface treatments, such as sand-blasting, scoring, polishing and grinding can increase surface roughness of the implants and improve the bonding strength between the coatings and metal substrate. For similar purposes, chemical surface treatments may be also applied to metal substrates prior to coating. Among others chemical treatments available for metals, acid etchings will be preferred by treating implantable devices with strong mineral acids, such as hydrofluoric, hydrochloric, sulfuric, nitric and perchloric acids. It may also useful to treat the metal devices with oxiding agents such as nitric acid, peroxyhalogen acids, hydroxyperoxides, or hydrogen peroxide to form a fresh metal oxide layer. After the mechanical or chemical treatment, it is necessary to rinse the implants with pure water under ultrasounds for removal of surface contaminants.

The method for coating medical implants with bioactive carbonated calcium phosphate layers consists of soaking medical implants into calcifying solutions at low temperature. This simple method is based on the finding that calcium phosphates are more soluble in mildly acidic medium than at neutral and even basic pH. Thus, aqueous solutions of calcium and phosphate ions can be more concentrated at mildly acid than at neutral pH. In other words, calcium phosphates precipitate at neutral or basic pH while they remain soluble at mildly acidic pH from a solution having the same concentrations of salts.

An increase of pH in the solution can induce the following stages: under-saturation, super-saturation or the formation of a meta-stable state, nucleation and crystal growth. Calcium phosphate nuclei can form onto a substrate—heterogeneous nucleation—when a solution has reached the super-saturation limit or the meta-stable state. At the super-saturation state, crystals can subsequently grow from meta-stable fluids. At higher saturation, homogeneous nucleation or precipitation in the solution is the predominant process. This invention makes use of pH changes to control the above stages and to induce the deposition of carbonated calcium phosphate layers on the surface of medical implants.

The above object can be achieved by bubbling a gaseous weak acid, preferably carbon dioxide gas, into a calcifying solution in order to decrease pH and thereby to increase the solubility of calcium phosphate salts. It is well known that natural sparkling water has a mildly acidic pH resulting from dissolved carbon dioxide gas. It is also an important feature that the pH of mineral water slowly increases to neutral or slightly basic pH during the natural release or exchange of dissolved carbon dioxide gas with air.

Figure 2:
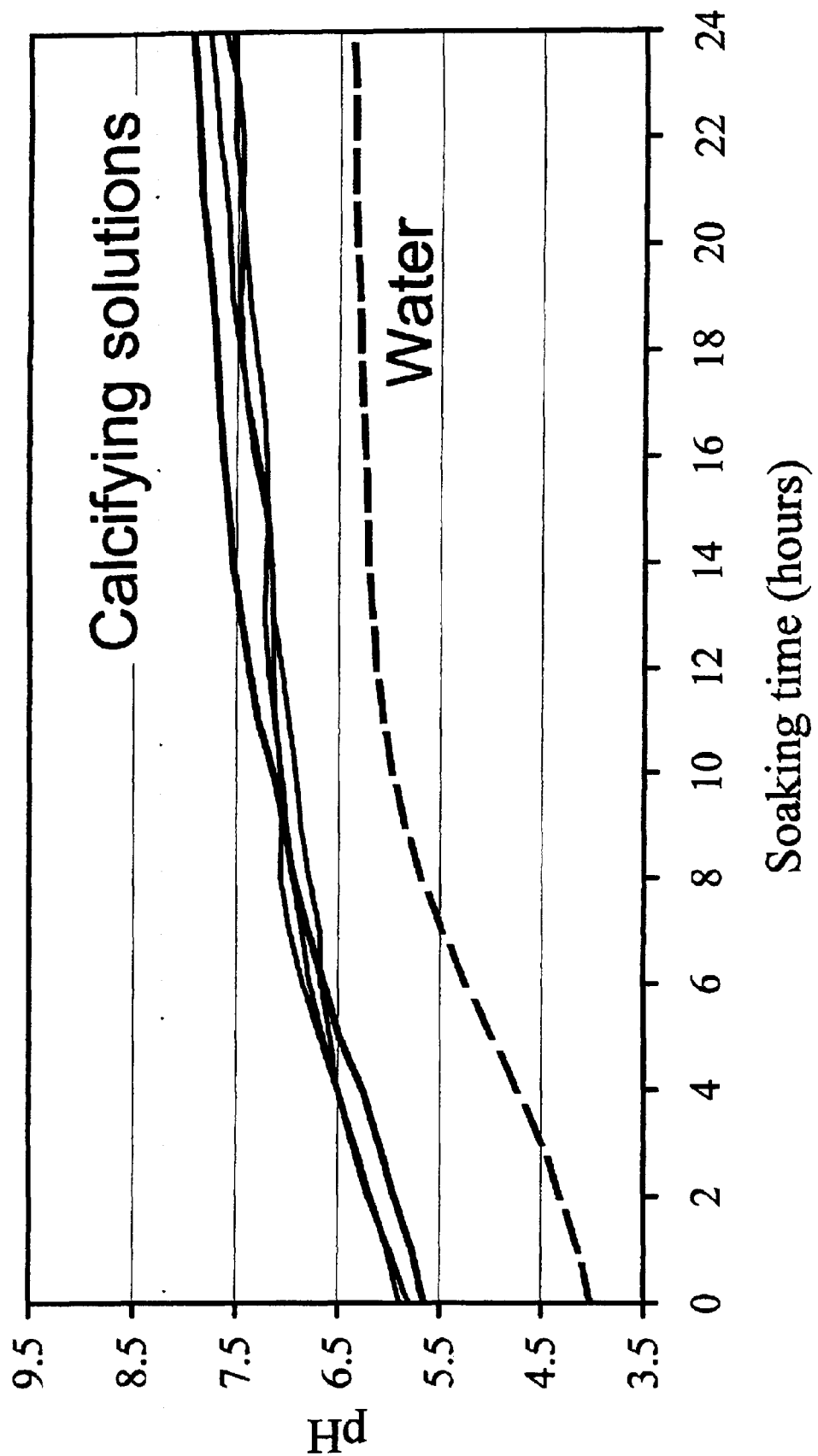

In a number of preferred embodiments, the bubbling of carbon dioxide gas into the calcifying solution is required. Carbon dioxide gas will dissolve in the calcifying solution and form hydrogen carbonate ions in water (equation (1) and (2)). The said medical implants are placed into an aqueous calcifying solution in which a gaseous weak acid, such as carbon dioxide gas, is passed through to produce a weakly acidic media. The initial pH of said calcifying solution is maintained in the range 3–7, preferably about 5.5 to 6.5 by bubbling $CO_2$ gas (FIG. 2). The carbon dioxide gas is introduced into the solution at a sufficient pressure to continuously generate bubbles. The pressure of $CO_2$ gas will be in the range 0.1–10 bars, preferably within 0.5 to 1.5 bars, more preferably about 1 bar.

In a preferred embodiment, the bioactive carbonated calcium phosphate coatings on medical implants are produced into an improved bioreactor or fermentor system (FIG. 1). A modified bioreactor system for culturing cells or micro-organisms is used for coating medical implants with bioactive carbonated calcium phosphate layers. The bioreactor should be made of borosilicate glass or stainless steel coated with Teflon™ to avoid deposition or incrustation of carbonated calcium phosphate on the inner side walls. The volume of the bioractor can range within 1 to 500 liters, more preferably from 1 to 150 liters depending on the number of medical implants to be coated. The use of a double-jacketed bioreactor vessel ensures a constant temperature in the calcifying solution. The temperature is controlled by a thermocouple linked to a thermo-circulator capable of cooling and heating at the desired temperature. The implants like hip stems or acetabular cups and the like are hold by special hooks fixed on the head-plate of the bioreactor. Several medical implants can be coated with the bioactive carbonated calcium phosphate layers in the same batch. The pH of calcifying solution is measured with a sterilizable combined glass electrode. The pH values are measured as a function of time. The bioreactor is equipped with a magnetically coupled stirring system. A gas-inlet pipe and a porous sparger are provided for producing tiny $CO_2$ gas bubbles into the calcifying solution and thus increases the gas exchange surface or aeration of the calcifying solution. An electro-valve or solenoid valve controls the flow of carbon dioxide gas introduced into the bioreactor. The flow of carbon dioxide gas can be regulated as a function of time or pH. The bioreactor vessel should have an aperture to avoid increasing the internal pressure and to allow the natural release of carbon dioxide gas out of the calcifying solution. The head-plate of bioreactor is equipped with an outlet condenser to prevent evaporation in the calcifying solution. All the critical parameters, like pH, temperature, carbon dioxide flow, calcium, phosphate and carbonate concentrations can be measured, recorded and controlled by an automated system (controller) as a function of time. Prior to applying the coating, the bioreactor and implants can be sterilized by autoclaving under water steam. The usual sterilization procedure consists of autoclaving the bioreactor, accessories and implants in a steam at 121° C. for 30 minutes. All the accessories mounted to the head-plates are isolated with O-ring joints and filters to maintain sterility during the coating process.

In the method according to the invention, the presence of magnesium, calcium and phosphate ions in the calcifying solution is essential. Particularly, the presence of magnesium has been found to be important for controlling the crystal growth of the coating during deposition from the calcifying solution. An optimum control of crystal growth leads to a uniform, strong and wear resistant coating. Particularly, the attachment of the coating to the substrate is beneficially effected by the presence of magnesium ions in the calcifying solution. A coating prepared according to the invention, preferably has crystals having a size in the submicrometer range. In a preferred embodiment, additional inhibitors of crystal growth, such as carbonate ions, may be incorporated in the calcifying solutions. If required, counter ions, like sodium and chloride might also be present to provide a constant ionic strength.

Preferably, the calcifying solution is prepared while the gaseous weak acid is bubbled through, in order to avoid precipitation. The introduction of the gas decreases the pH of the solution and allows the complete dissolution of the magnesium, calcium and phosphate, and possible other salts. Preferably, the bubbling is started at least 5 minutes before, and during, the addition of the salts. Thus, the pH is lowered to approximately 3–8, more preferably to 5.5–6.

Of course it is also possible to start the bubbling with the gaseous weak acid after the addition of the desired amounts of the salts to the solution. Once the bubbling is started, in accordance with this embodiment, it is important to ensure that the salts dissolve completely.

The calcifying solution is preferably prepared with ultra pure water and pure grade chemicals. The calcifying solution is preferably filter sterilized through a 0.2 microns filter membrane, prior to being pumped into the bioreactor. The molar calcium to phosphorus ratio in the calcifying solution is generally within the range 1–3, more preferably between 1.5 to 2.5. The concentrations of the ions in the calcifying solution are chosen such, that in the absence of the gaseous weak acid, the solution is super-saturated or oversaturated. The molarity of the calcium source will generally be in the range 0.5–50 mM, preferably about 2.5 to 25 mM. The phosphate source will generally be from about 0.5 to 20 mM, more preferably about 1 to 10 mM. The concentration of magnesium in the calcifying solutions will usually be within the range 0.1–20 mM, more preferably about 1.5 to 10 mM. The carbonate concentration will range from 0 to 50 mM, more preferably 0 to 42 mM. The ionic strength will be within the range 0.10–2 M, more preferably in between 0.15 to 1.5 M. The calcifying solution is preferably stirred to approximately 10–1000 rpm, more usually 50 to 200 rpm. The temperature is maintained at about 5–80° C., preferably in the range of about 5–50° C.

The carbon dioxide has a limited solubility in aqueous solutions. In contact with air, a carbonated aqueous solution is free of $CO_2$ or completely degassed within few hours depending on the surface of solution in contact with air. In the open bioreactor described herein, the complete exchange of dissolved $CO_2$ gas with atmosphere takes approximately 8 to 48 hours, more preferably between 12 to 24 hours. The natural release of $CO_2$ gas causes the pH of the remaining solution to increase (FIG. 2). In others words, saturation in the calcifying solution can increase until the precipitation of the bioactive layers on the surface of implantable materials occurs. Optionally, air can be bubbled through the solution to degas or aerate the solution and accelerate the escape, release or exchange of the gaseous weak acid. The initial and final pH values as well as pH changes with time depend on the amount of carbonate and phosphate salts added to the calcifying solution. The buffering capability can be adjusted to a desired pH value by adding more or less of phosphate and carbonate salts. The pH can be maintained within the desired range by introducing carbon dioxide gas. In essence, the flow of carbon dioxide can be adjusted by using an electro or selenoid valve piloted by the controller. During the natural release of $CO_2$ gas out of the calcifying solution, the pH will increase to about 6–10, more preferably about 7.5 to 8.5 after soaking for 24 hours. The carbonated calcium phosphate layer will precipitate on the surface of implantable devices at a pH value of within about 6.5–7.5. The said precipitation on the surface of medical implants is related to a heterogeneous nucleation step. The carbonated calcium phosphate crystals might subsequently precipitate into the calcifying solution by a crystal growth process. In the invention, the heterogeneous nucleation is favored by the energetic stabilization of nucleus on the substrate. The high density of nucleation ensures a uniform deposition of carbonated calcium phosphate crystals onto the surface of medical implants. The above process can be illustrated by the following equations:

$$CO_2(g) \leftarrow\rightarrow CO_2(aq) \quad (1)$$

$$CO_2(g)+H_2O \leftarrow\rightarrow HCO_3^- + H^+ \quad (2)$$

$$10Ca^{2+}+6PO_4^{3-}+2OH^- \rightarrow Ca_{10}(PO_4)_6(OH)_2\downarrow \quad (3)$$

The process of bubbling carbon dioxide gas into the aqueous calcifying solution and escape of the carbon dioxide gas from the solution can be repeated to deposit a subsequent layer of carbonated calcium phosphate minerals on the implantable material. In a method according to the invention, it may be essential to control the pH and thereby the nucleation stage by bubbling $CO_2$ gas for various time. The bubbling time is usually comprised between a few seconds to minutes, preferably about 1 to 600 seconds. The introduction of carbon dioxide causes a decrease of pH while the pH of calcifying solution has a tendency to increase naturally without bubbling $CO_2$ gas. The increase of pH may be due to the natural exchange of $CO_2$ gas with atmosphere and the buffering capability of the calcification solution. By adjusting the time and flow of $CO_2$ gas introduced into the calcifying solution, the pH can oscillate around a value ranging from 6 to 9, more preferably the pH of the calcifying solution can be maintained between 6.5 to 7.5. This pH oscillation is correlated to the nucleation stage of carbonated calcium phosphate crystals on the surface of medical implants. A high density of nucleation is thereby provided and carbonated calcium phosphate crystals can nucleate and grow onto the surface of medical implants. Homogeneous layers can uniformly deposit on the implant substrate. The total thickness of layers will preferably be within the range 0.5–100 microns, more likely 0.5 to 50 microns. While the layers are thin, usually below 5 microns, the coatings can diffract the natural light forming colored fringes ranging from blue to red colors. This diffraction of light is similar to the phenomenon that may be observed when a drop of oil is present on water. For higher thickness, the layers give a shiny gray or white coloration.

The thin carbonated calcium phosphate layers can induce the precipitation of subsequent layers by immersion into a second calcifying solution. In other words, the thin carbonated calcium phosphate layers can serve as seed crystals for subsequent layers. The second calcifying solution is preferably super-saturated with respect to hydroxyapatite. Under the super-saturation conditions, crystal growth may take place, and thick, crystalline and uniform calcium phosphate layers can be produced onto the surface of a medical implant. The second calcifying solution should contain calcium and phosphate salts with only small amounts of, or even without, inhibitors of crystal growth, like magnesium or carbonate. As the second, or further layer will be deposited on a calcium phosphate coating (the first layer), a good attachment is more easily achieved.

The second calcifying solution can be prepared in the absence or presence of a gaseous weak acid, such as carbon dioxide. Preferably, the second calcifying solution is buffered at a physiological pH, around 7.4, with an appropriate buffer, like tris(amino-ethane) and diluted with hydrochloric acid. The concentration of calcium ions in the second calcifying solution may range from 0.5 to 10 mM, more preferably from 0.5 to 5 mM. The concentration of phosphate may range from 0.5 to 6 mM, more preferably from 0.5 to 3 mM. Magnesium and carbonate ions are preferably present in concentrations below 1 and 5 mM, respectively. More specifically, magnesium might be present in an amount between 0.1 and 3 mM, more preferably between 0.5 and 1.5 mM. Sodium chloride, or any suitable salt may be added to maintain the ionic strength of the second calcifying solution at a value of 0.05 to 0.5 mM, preferably 0.1 to 0.2 mM.

The composition and crystal size of the layers will be strongly dependent on the amount of crystal growth inhibitors in the calcifying solutions.

In a preferred embodiment, the layers will be composed of hydroxyl carbonate apatite with a poor crystallinity or amorphous calcium phosphates containing magnesium and carbonate ions. Depending on the ion concentrations and pH of the calcifying solution, a coating of a compound having the general formula (I) can be obtained:

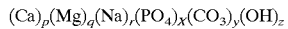
$$(Ca)_p(Mg)_q(Na)_r(PO_4)_x(CO_3)_y(OH)_z \qquad (I)$$

with p>1 and x, y and z>0
and in which 2p+2q+r=3x+2y+z

A series of salts having the general formulae (I) can be coated to medical devices. For example, if p=10, q=0, r=0, x=6, y=0 and z=2, the above formulae gives the structural formula of hydroxy apatite $Ca_{10}(PO_4)_6(OH)_2$ with a calcium to phosphorus ratio of 1.67. If 8<p<10 and 4<x<6, series of calcium deficient apatite resembling to bone mineral are obtained. The coating may be also composed of octacalcium phosphate (OCP) with the formulae $Ca_8H_2(PO_4)_{6.5}H_2O$ which is involved in the early stage of biomineralization of calcified tissues. If p=1 and y=1, the formula represents calcium carbonate $CaCO_3$ having calcite, vaterite, aragonite structure or a combination thereof.

The chemical composition of the coating can be variable but the layers always contain magnesium, calcium and phosphate ions. If desired carbonate ions may be also incorporated within the coating, additionally the film can include traces of sodium and chloride ions. The amount of calcium and phosphorus will average between 20 to 40 and 10 to 30 weight percent, respectively. The magnesium and carbonate contents in the coating will be within the range of 0.1–5 weight percent and 0–7 weight percent, respectively. The metal to phosphorus ratio (M/P with M=Ca+Mg+Na) will be within the range 1.00 to 2.00, more preferably in between 1.30 to 1.80.

The present coatings may incorporate a wide variety of biologically active agents, such as peptides, growth factors, bone morphogenetic proteins, combinations thereof, and the like. The growth factors will be co-precipitated within the layers on the surface of implantable devices and may serve as drug delivery systems. The gradual release of growth factors around the coated article can stimulated osteoblasts cells and enhance bone healing. Furthermore, antibiotics like tobramycin, vancomycin, and the like can be also precipitated within the coatings to prevent infection post-surgically.

Generally, the growth factors and antibiotics will be solubilised in the calcifying solutions at a concentration of 1 μg/ml to 1 mg/ml.

The coating process described herein can deposit a variety of calcium phosphate compounds containing carbonate and others ions on the surface of an implantable device. The layers will be similar in composition and crystallinity with bone and teeth minerals and have desired bioresorbability, bone-bonding properties to improve the biological fixation of medical devices to living calcified tissue.

It has further been found, that coatings on medical implants, prepared in a biomimetic approach, such as the present process, have osteoinductive properties. A biomimetic approach concerns a process resulting in a calcium phosphate coating that, to a certain extent, mimics calcium phosphates resulting from biological mineralization processes, such as in bone or sea shells. This means that a biomimetic process often takes place at ambient temperature and results in a calcium phospate that resembles one, or a combination of the numerous naturally occurring calcium phosphate compositions. A biomimetic coating may be prepared employing a solution that is rich in at least calcium and phosphorous ions, either or not in physiologic concentrations, and optionally in the presence of nucleation promoting agents, such as bioactive glass particles. Examples of biomimetic approaches include the process as described herein, but also those described by Kokubo (see EP No. 0 389 317 A1 and NP No. 0 678 300 A1).

It has now been found that a biomimetic approach leads to a specific reactivity (e.g. dissolution-reprecipitation of calcium phosphate or adsorption of endogenous biologically active agents, such as BMP's), biological conversion after implantation, morphology, surface (micro)structure and/or implant porosity of the coating, which induces formation of bone cells, such as osteoblasts, from progenitor cells even when the implants are provided in vivo in non-bony tissues. It has further been found, that the present process for providing a coating on a substrate leads to a particular morphology and crystal orientation, that increases the osteoinductive character of the biomimetic coating. Further, certain coatings having specific chemical compositions, such as OCP coatings, lead to even greater osteoinductive effects.

This invention is illustrated by the following examples but should not be construed to be limited thereto. In the examples, the percentages are expressed in weight unless specified otherwise.

EXAMPLE 1

Figure 3:
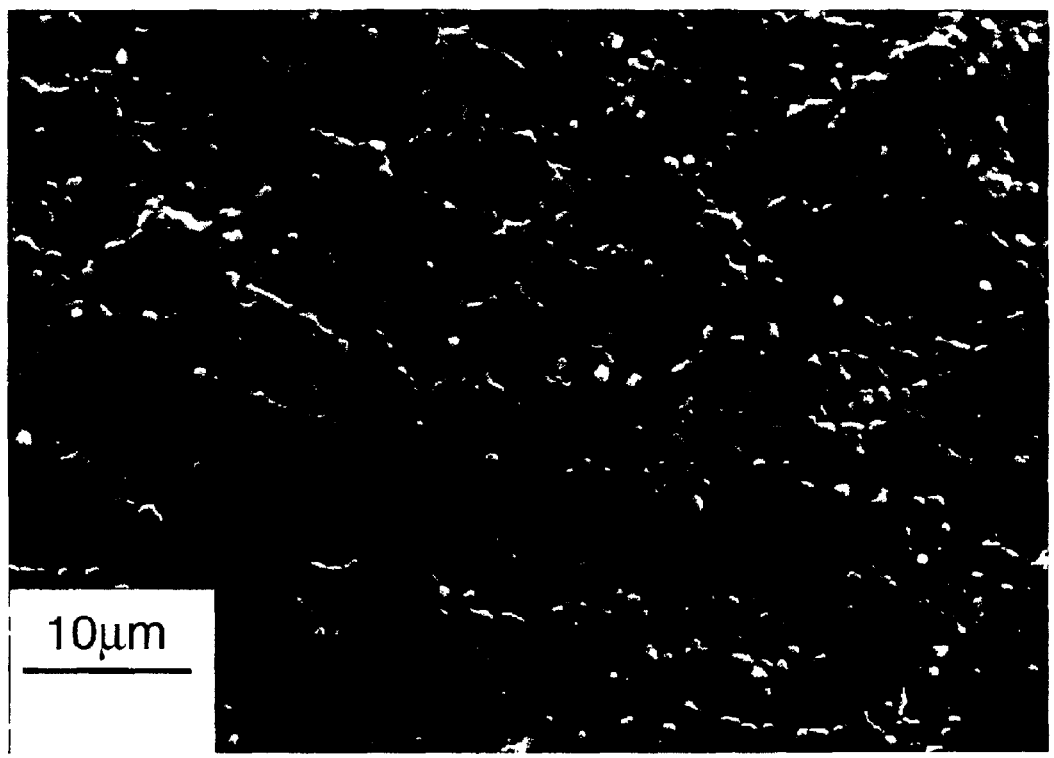
Figure 4:
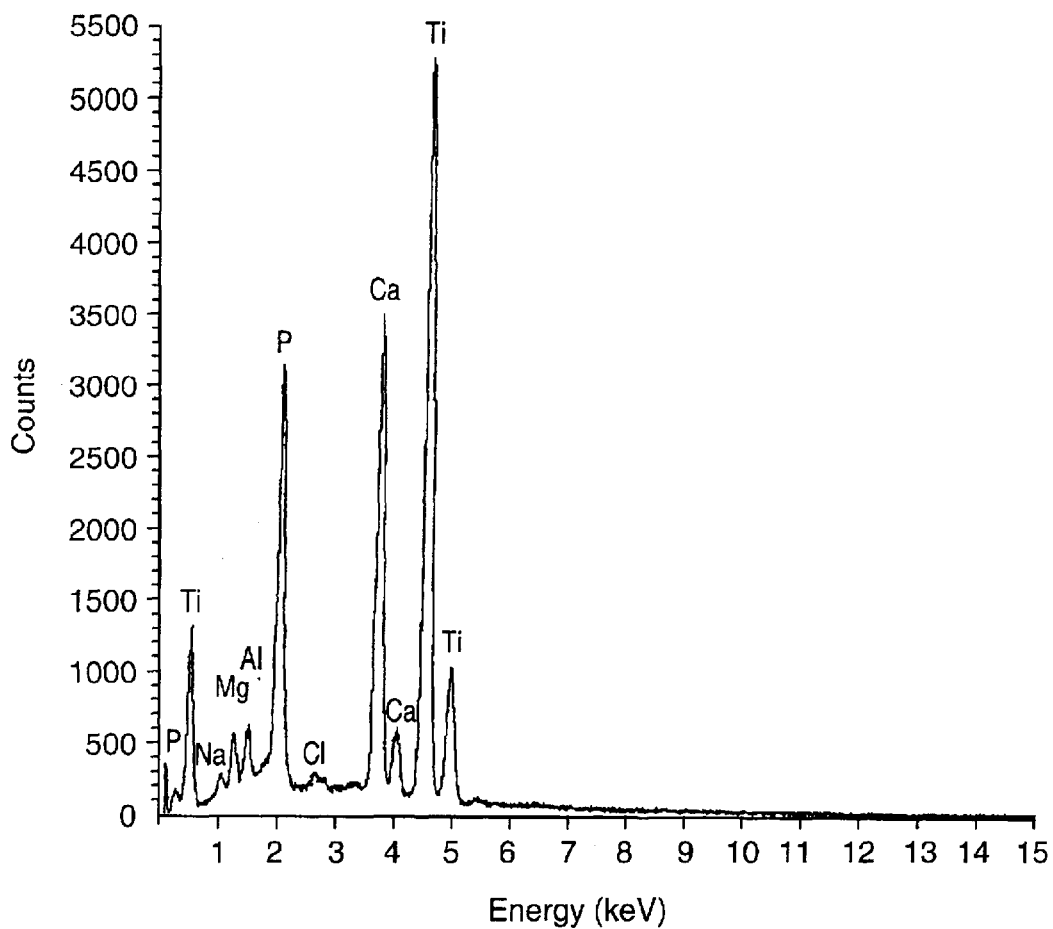
Figure 7:
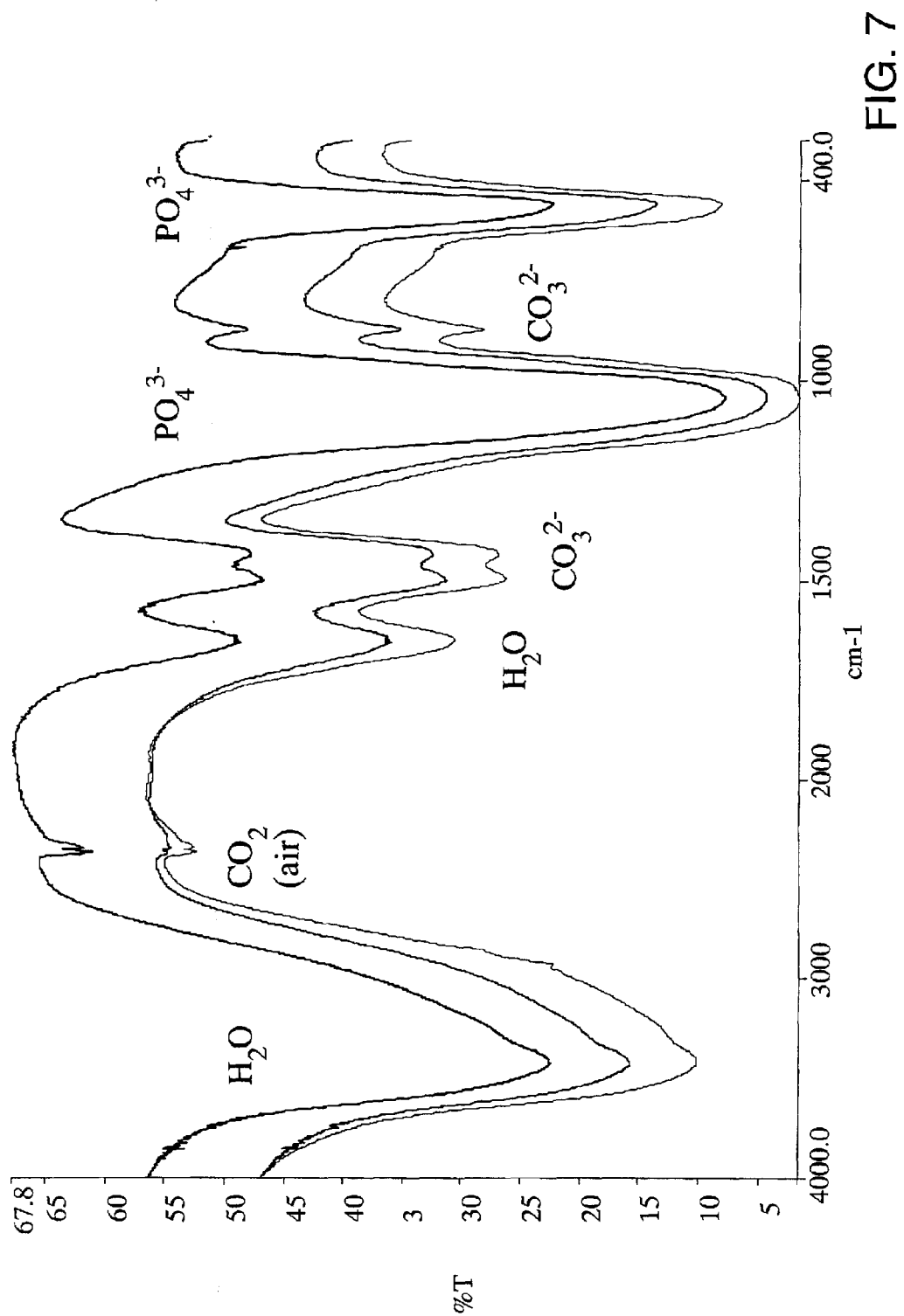
Figure 8:
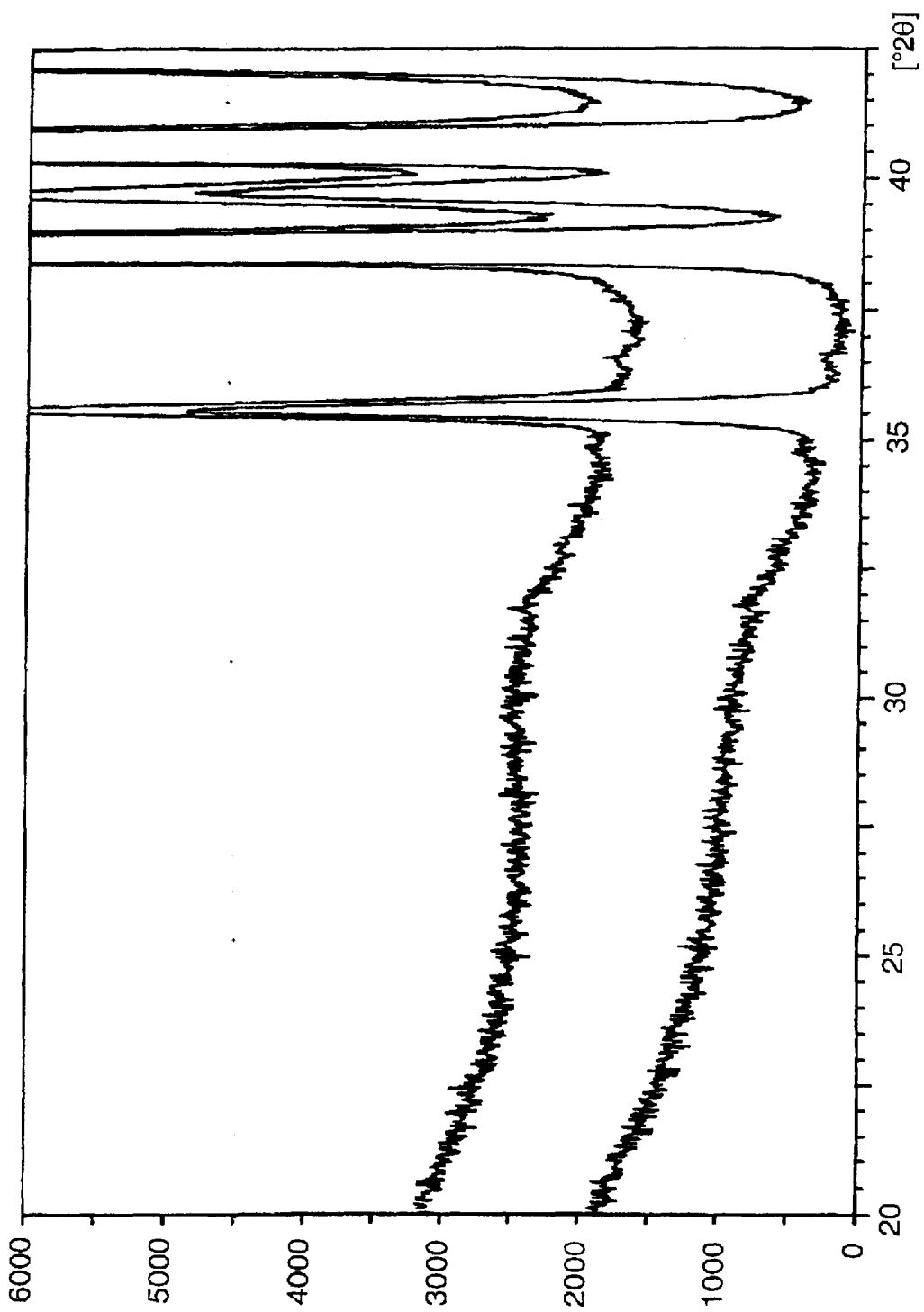

Pieces of titanium alloy are cut from a sheet of commercially available Ti6Al4V foil or rods. Ti6Al4V plates of 10×10×2 mm and cylinders of 5 mm in diameter and 10 mm in length are used. Ti6Al4V wires of 1 mm in diameter are also coated with the bioactive carbonated calcium phosphate layers. Prior to coating, the implants are sand- or grit-blasted to increase their surface roughness. The implants are ultrasonically cleaned for 15 min in acetone, then ethanol (70%) and finally pure water. The Ti6Al4V plates are then etched for 30 min in an ultrasonic cleaner with a concentrated acid mixture containing distilled water, hydrochloric acid (HCl, 36%) and sulfuric acid ($H_2SO_4$, 96%) with a volume fraction of 2:1:1. A soft etching procedure can be alternately applied by soaking the implants into a mixture made of 994 ml of pure water, 2 ml of hydrofluoric acid (HF, 40%) and 4 ml of nitric acid ($HNO_3$, 50%). The etched Ti6Al4V plates were thoroughly washed with pure water. After etching and rinsing, all samples are placed into a 3 liters insulated bioreactor and sterilized with stem at 121° C. for 30 minutes. The calcifying solution is prepared by dissolving 40.00 g of NaCl (99.9%) 1.84 g of $CaCl_2.2H_2O$ (99.9%) 1.52 g of $MgCl_2.6H_2O$ (99.9%) 1.06 g of $NaHCO_3$ (99%) and 0.89 g of $Na_2PO_4.2H_2O$ (99.9%) in 1000 ml of pure water. The calcifying solution is pumped through a 0.2 microns membrane filter into the bioreactor. Carbon dioxide gas is introduced into the solution at a pressure of 0.5–1.5 bar generating $CO_2$ bubbles. The pH of the solution is measured with an electrode and continuously monitored. The solution is maintained at pH 5.5–6.5 by the introduction of $CO_2$ gas. The temperature is controlled to 37° C. by using a thermocouple and a heating device. The calcifying solution is continuously stirred at 100 rpm. he flow of $CO_2$ gas is stopped and the pH starts to increase slowly. After soaking for 24 hours, the pH of calcifying solution is within the range 7.8–8.6. After coating, the samples are ultrasonically cleaned in demineralised water for 10 minutes and dried at 50° C. for several hours. The thickness of the bioactive layers is measured by using Eddy-Current instruments. The coating has a thickness averaging between 1 to 5 microns. The tensile bonding strength of the layers onto the substrate average between 40 to 65 Mpa. The morphology and composition of coating are evaluated by using SEM together with XRMA (FIGS. 3 and 4). Dense and uniform carbonated calcium phosphate layer are observed on the surface of implants. The layers are composed of micrometer sized globules or spherules containing Ca, O, P, and traces of Mg, Na and Cl (FIG. 3). FT-IR spectra and TF-XRD determine the crystallinity of the coatings. The FT-IR spectra (FIG. 7) show featureless and wide carbonate and phosphate bands typical of poorly crystallised hydroxyl cabonate apatite similar to bone mineral. The TF-XRD patterns (FIG. 8) indicate the diffraction lines of the Ti6Al4V substrate and halo or bump located at around 30 degrees (2 theta) characteristic of amorphous calcium phosphate or poorly crystallised hydroxyl carbonate apatite phase. For implantation purposes, the coated devices are sterilized by steam at 121° C. for 30 minutes.

EXAMPLE 2

Figure 5:
Figure 6:
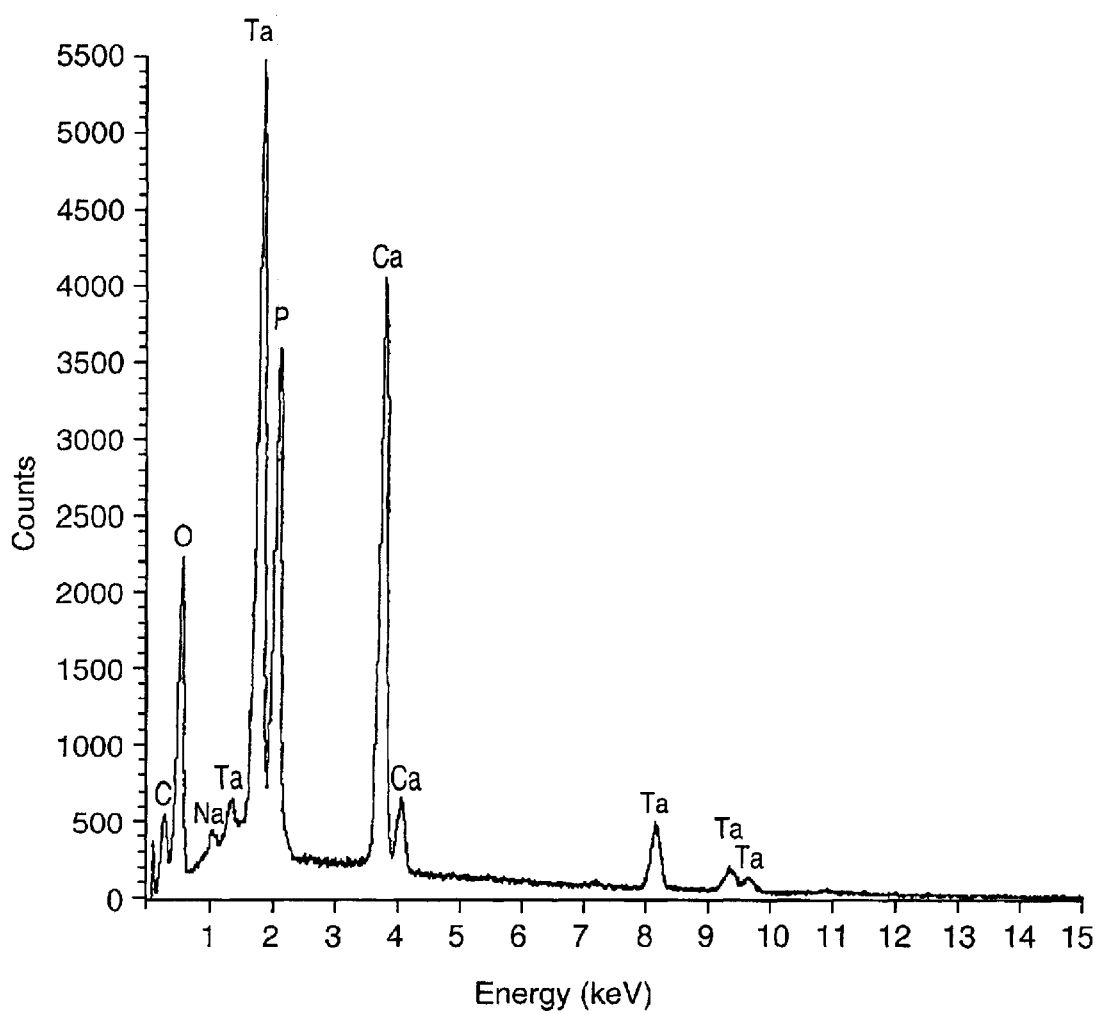

Porous tantalum implants (Hedrocel™, Implex Corporation, Allendale, N.J.) of respectively 2.5 and 5 mm in diameter and 5 and 10 mm in length are used. The implants are ultrasonically cleaned for 10 minutes in acetone, ethanol (70%) and finally pure water. The implants are then placed into meshed bags and hold into the bioreactor system. After autoclaving, the implants are soaked into a calcifying solution as described in example 1. After coating, the coated devices are ultrasonically rinsed with pure water and sterilized with an autoclave. The SEM observations and EDAX analyses confirm the uniform deposition of a well-attached dense calcium phosphate layer on and into the porous tantalum implants (FIGS. 5 and 6).

COMPARATIVE EXAMPLE 3

Three Ti6Al4V plates were successively cleaned in acetone, ethanol, and demi water. Next, the plates were etched, using a mixture of hydrochloric acid and sulfuric acid, and thoroughly rinsed with demi water.

A calcifying solution was prepared by dissolving 40.0 g of NaCl, 2.95 g of $CaCl_2.2H_2O$ and 1.80 g of $Na_2HPO_4.2H_2O$ in 1000 ml demi water, while bubbling carbon dioxide gas through the solution at a pressure of 0.5–1.5 bar.

Figure 9:
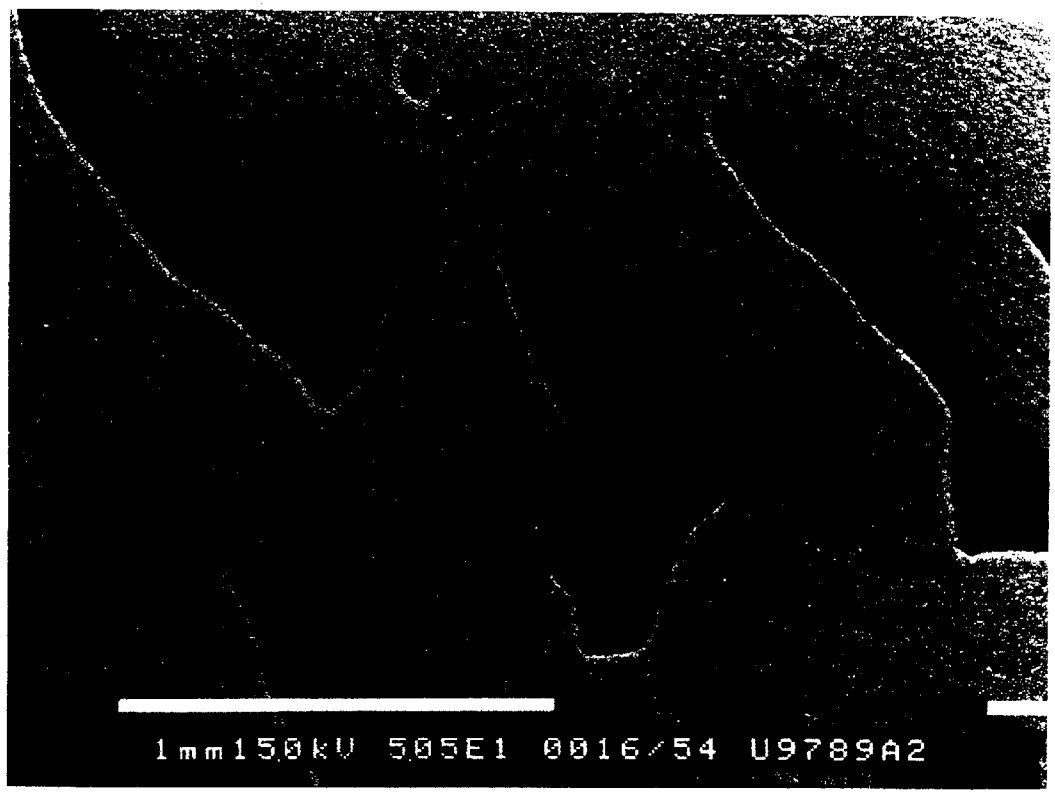

The Ti6Al4V plates were soaked at 37° C. for 24 hours in the calcifying solution, and finally rinsed with demi water. A calcium phosphate layer was found to partially cover the plates. As can be seen from FIG. 9, the coating was not uniformly deposited on the surface of the substrates. It was found that the coating was not well attached to the Ti6Al4V surface of the substrates, and could be easily removed or scraped off.

EXAMPLE 4

Porous tantalum cylinders were coated in a procedure analogous to that of example 1. After soaking in the calcifying solution (which had the same composition as the calcifying solution in example 1), a thick and crystalline biomimetic layer covered the tantalum cylinders evenly. The layer was composed of octacalcium phosphate (OCP, $Ca_8(HPO_4)_2(PO_4)_4.5H_2O$) crystals aligned perpendicularly from the surface of the substrate, as determined by SEM on a cross-sectioned cylinder.

EXAMPLE 5

Animal Experiments

The protocol provides for the evaluation, safety and effectiveness of the bioactive layers applied to different biocompatible substrates such as Ti6Al4V, porous tantalum and polyactive implants in vivo. The bone-conducting ability and bone in-growth of the bioactive layers are evaluated by using several animal models. Conventional histology techniques are used to compared bare and coated implants. The experiments and substrates are not limited hereto.

Intra-femoral Implantation in Rats:

Four Ti6Al4V wires coated as described in example 1 or non-coated with the bioactive carbonated calcium phosphate are press-fit implanted in the femur of rats (Fisher, F344, adult male, 200–250 g) for 4 weeks. After sacrifice, the femoral bone and implants are retrieved, rinsed with phosphate buffered solution, dehydrated and embedded in resin (PMMA). The bone and coated implants are stained with alizarin and cross-sectionned into histology slides. The surface of bone in contact with the coating is observed by light microscopy and measured by image analyses. The bone conducting ability of the coating is compared to bare implants.

Intra-cortical Implantation in Goats:

After sterilization, the coated, as described in example 2, or non-coated porous tantalum implants (5 mm diameter and 10 mm long) are implanted into the femoral bone of mature goats. The implants are inserted in both proximal and distal regions of the femurs. 6 coated or bare implants are used per goat. After implantation for 2, 4, 8 and 16 weeks, the animals are sacrificed and the bones are retrieved. The bones are then washed with phosphate buffer solution, dehydrated with series of ethanol and embedded in PMMA. The bones are cross-sectioned by using a microtome sawing machine. The implants surrounded by bone are then carbon sputtered for SEM observations. The total bone in-growth within the porous tantalum implants is observed by back-scattering scanning electron microscopy and measured by using image analyses techniques. The total bone in-growth of coated porous tantalum implants is finally compared to bare implants. The results of the study indicate a mean bone in-growth of 35% for porous tantalum alone and 80% for implants coated with the bioactive layers after 8 weeks in vivo. These results show a two-fold increase in bone in-growth for implants coated with the bioactive layers.

Intra-muscular Implantation in Dogs:

After sterilization, implants coated with an OCP layer as described in example 4, and non-coated porous tantalum cylinders (5 mm diameter and 10 mm long) are implanted into the thigh muscles of mature dogs (body weight about 20 kilograms). From each implant type, eight (8) cylinders are implanted (one per dog) and the survival time is three months. Surgery is performed under general anaesthesia and sterile conditions. Briefly, a longitudinal skin incision is made in the leg and the thigh muscle is exposed by blunt dissection. A longitudinal incision is made in the muscle fascia after which an intramuscular pocket is created in which the implant is inserted. The incision is sutured with a fine silk thread to keep the implant inside the muscle pouch, the skin is closed with a silk suture and the wound is cleaned with iodine tincture. After three months, the dogs are terminated with an intra-abdominal injection of pentobarbital and the implants are collected with surrounding tissues and labelled as indicated before they were implanted. All samples are subsequently fixed in 10% buffered formalin at 4° C., dehydrated through a graded series of ethanol to ethanol 100% and embedded in methyl methacrylate (MMA). Undecalcified sections are made on a modified innerlock diamond saw and examined by light microscopy.

Histological analysis of the sections reveal that the uncoated Tantalum cylinders are surrounded and invaded with fibrous tissue, while de novo bone formation is absent. In contrast, the OCP coated porous Tantalum cylinders reveal abundant de novo formed bone that is in direct contact with the OCP coated implant surface. Almost the entire surface of the OCP coated porous cylinders is coated with a layer of bone. These unique results clearly indicate that a biomimetic coating, in this example composed of OCP crystals that are oriented perpendicular to the implant surface, can induce bone formation in a non-bony environment. Coating composition, reactivity (e.g. dissolution-reprecipitation of calcium phosphate or adsorption of endogenous biologically active agents, such as BMP's), biological conversion after implantation, morphology, surface microstructure and/or implant porosity can be responsible for the osteoinductive property of the implant by inducing the differentiation of progenitor cells into osteogenic cells.

What is claimed is:

1. A coated implant comprising an implant and a coating, wherein said coating comprises an amorphous layer contacting the implant, wherein said amorphous layer comprises a deposit of crystals nucleated directly onto the implant from a solution and comprises magnesium ions, calcium ions, and phosphate ions, and a crystalline layer contacting the amorphous layer, wherein said crystalline layer comprises calcium and phosphate ions, and wherein said coating has an average bond strength to the implant of between 40 to 65 Mpa, and induces formation of bone cells from progenitor cells.

2. The implant of claim 1 wherein said implant is formed from one or more of metal, organic material, polymer, or ceramic.

3. The implant of claim 1 wherein the implant is treated by a mechanical or chemical surface treatment before said coating is applied to said device.

4. The implant of claim 3 wherein the implant is treated by sand-blasting, scoring, polishing, or grounding.

5. The implant of claim 3 wherein the implant is treated by contacting with strong mineral acid or an oxidizing agent in a manner to etch the implant.

6. The coated implant of claim 1, said coating further comprising one or more ions selected from the group consisting of hydroxide, carbonate, chloride, sodium and potassium.

7. The coated implant of claim 1, said coating comprising one or more of amorphous carbonate calcium phosphate, hydroxyapatite, calcium deficient apatite, hydroxyl carbonate apatite, octacalcium phosphate, dicalcium phosphate dihydrate or calcium carbonate.

8. The coated implant of claim 1 wherein the coating has a thickness of about 0.5 to about 100 microns.

9. The coated implant of claim 1 wherein the coating has a thickness of about 0.5 to about 50 microns.

10. The coated implant of claim 1, wherein said amorphous layer induces formation of bone cells from progenitor cells.

11. The coated implant of claim 1 wherein the crystalline layer comprising calcium and phosphate ions further comprises octacalcium phosphate.

12. The coated implant of claim 1 wherein the coating comprises octacalcium phosphate.

13. A coated implant comprising an implant and a coating, wherein said coating comprises an amorphous layer contacting the implant, wherein said amorphous layer comprises a deposit of octacalcium phosphate crystals nucleated directly onto the implant from solution, and a crystalline layer contacting the amorphous layer, wherein said crystalline layer comprises calcium and phosphate ions, and wherein said coating has an average bond strength to the implant of between 40 to 65 Mpa, and induces formation of bone cells from progenitor cells.

14. The implant of claim 13 wherein said implant is formed from one or more of metal, organic material, polymer, or ceramic.

15. The implant of claim 13 wherein the implant is treated by a mechanical or chemical surface treatment before said coating is applied to said device.

16. The implant of claim 13 wherein the implant is treated by sand-blasting, scoring, polishing, or grounding.

17. The implant of claim 13 wherein the implant is treated by contacting with strong mineral acid or an oxidizing agent in a manner to etch the implant.

18. The coated implant of claim 13 wherein the coating has a thickness of about 0.5 to about 100 microns.

19. The coated implant of claim 13 wherein the coating has a thickness of about 0.5 to about 50 microns.

* * * * *